US 6,702,787 B2

(12) United States Patent
Racenet et al.

(10) Patent No.: US 6,702,787 B2
(45) Date of Patent: Mar. 9, 2004

(54) TROCAR SEAL SYSTEM

(75) Inventors: David C. Racenet, Southbury, CT (US); Gene A. Stellon, Southington, CT (US); William J. Vumback, Northford, CT (US); Joseph Pasqualucci, Southbury, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 62 days.

(21) Appl. No.: 10/165,373

(22) Filed: Jun. 6, 2002

(65) Prior Publication Data
US 2002/0156432 A1 Oct. 24, 2002

Related U.S. Application Data

(63) Continuation of application No. 09/527,955, filed as application No. PCT/US98/08968 on Mar. 9, 2000.
(60) Provisional application No. 60/045,412, filed on May 2, 1997.

(51) Int. Cl.[7] .................................. A61M 5/14
(52) U.S. Cl. .................. 604/256; 604/167.06; 604/158; 604/164.01; 604/264
(58) Field of Search ........................ 604/167.01, 167.06, 604/256, 158, 164.01, 164.09, 164.1, 264, 272; 606/167; 137/874, 872, 861

(56) References Cited

U.S. PATENT DOCUMENTS

| 3,421,509 A | 1/1969 | Fiore |
| 3,565,078 A | 2/1971 | Vailliancourt et al. |
| 3,853,127 A | 12/1974 | Spademan |
| 3,907,310 A | 9/1975 | Dufour |
| 3,994,287 A | 11/1976 | Turp et al. |
| 4,000,739 A | 1/1977 | Stevens |
| 4,112,932 A | 9/1978 | Chiulli |
| 4,173,350 A | 11/1979 | Sieghartner |
| 4,177,814 A | 12/1979 | Knepshield et al. |
| 4,177,997 A | 12/1979 | Cartwright |
| 4,240,335 A | 12/1980 | Stucka et al. |
| 4,240,411 A | 12/1980 | Hosono |
| 4,311,315 A | 1/1982 | Kronenberg |
| 4,334,688 A | 6/1982 | Spargo et al. |
| 4,338,689 A | 7/1982 | Zieg |
| 4,386,756 A | 6/1983 | Muchow |
| 4,387,879 A | 6/1983 | Tauschinski |

(List continued on next page.)

FOREIGN PATENT DOCUMENTS

| DE | 3217118 | 8/1983 |
| EP | 0051718 | 5/1982 |
| EP | 0113520 | 7/1984 |
| EP | 0312219 | 4/1989 |
| GB | 1482857 | 8/1977 |
| WO | WO93/04717 | 3/1993 |
| WO | WO98/53865 | 12/1998 |

Primary Examiner—Ira S. Lazarus
Assistant Examiner—Tu Cam Nguyen

(57) ABSTRACT

A seal assembly for reception of an elongated surgical instrument is provided which includes a body having at least one opening configured and dimensioned to permit entry of an elongated surgical instrument and defining a central longitudinal axis; a seal member formed of a resilient material and defining an aperture therein, the aperture being configured and dimensioned such that insertion of the surgical instrument into the aperture causes the resilient material defining the aperture to resiliently contact the outer surface of the surgical instrument in a substantially fluid tight manner; and a fabric layer juxtaposed relative to the resilient material. A coating may be applied to the seal member to reduce friction between the seal member and surgical instrumentation inserted therein. The coating is preferably a hydrocyclosiloxane membrane prepared by plasma polymerization process.

18 Claims, 10 Drawing Sheets

U.S. PATENT DOCUMENTS

| | | | |
|---|---|---|---|
| 4,430,081 A | 2/1984 | Timmermans | |
| 4,447,237 A | 5/1984 | Frisch et al. | |
| 4,464,178 A | 8/1984 | Dalton | |
| 4,473,094 A | 9/1984 | Harris | |
| 4,553,760 A | 11/1985 | Reed et al. | |
| 4,588,195 A | 5/1986 | Antonini et al. | |
| 4,601,710 A | 7/1986 | Moll | |
| 4,626,245 A | 12/1986 | Weinstein | |
| 4,641,842 A | 2/1987 | Kataoka | |
| 4,654,030 A | 3/1987 | Moll et al. | |
| 4,655,752 A * | 4/1987 | Honkanen et al. | 604/256 |
| 4,673,393 A | 6/1987 | Suzuki et al. | |
| 4,705,511 A | 11/1987 | Kocak | |
| 4,715,360 A | 12/1987 | Akui et al. | |
| 4,723,550 A | 2/1988 | Bales et al. | |
| 4,758,225 A | 7/1988 | Cox et al. | |
| 4,842,591 A | 6/1989 | Luther | |
| 4,844,483 A | 7/1989 | Iijima et al. | |
| 4,844,484 A | 7/1989 | Antonini et al. | |
| 4,857,062 A | 8/1989 | Russell | |
| 4,869,717 A | 9/1989 | Adair | |
| 4,874,377 A | 10/1989 | Newgard et al. | |
| 4,874,378 A | 10/1989 | Hillstead | |
| 4,889,349 A | 12/1989 | Muller | |
| 4,909,798 A | 3/1990 | Fleischhacker et al. | |
| 4,917,668 A | 4/1990 | Haindl | |
| 4,929,235 A | 5/1990 | Merry et al. | |
| 4,932,633 A | 6/1990 | Johnson et al. | |
| 4,943,280 A | 7/1990 | Lander | |
| 4,960,412 A | 10/1990 | Fink | |
| 4,966,588 A | 10/1990 | Rayman et al. | |
| 4,998,740 A | 3/1991 | Tellier | |
| 5,000,745 A | 3/1991 | Guest et al. | |
| 5,002,557 A | 3/1991 | Hasson | |
| 5,015,000 A | 5/1991 | Perini | |
| 5,038,756 A | 8/1991 | Kepley | |
| 5,041,095 A | 8/1991 | Littrell | |
| 5,053,014 A | 10/1991 | Van Heugten | |
| 5,053,016 A | 10/1991 | Lander | |
| 5,064,416 A | 11/1991 | Newgard et al. | |
| 5,073,169 A | 12/1991 | Raiken | |
| 5,104,383 A | 4/1992 | Shichman | |
| 5,127,626 A | 7/1992 | Hilal et al. | |
| 5,137,520 A | 8/1992 | Maxon et al. | |
| 5,167,636 A | 12/1992 | Clement | |
| 5,180,373 A | 1/1993 | Green et al. | |
| 5,197,955 A | 3/1993 | Stephens et al. | |
| 5,201,714 A | 4/1993 | Gentelia et al. | |
| 5,209,736 A | 5/1993 | Stephens et al. | |
| 5,209,737 A | 5/1993 | Ritchart et al. | |
| 5,221,264 A | 6/1993 | Wilk et al. | |
| 5,226,891 A | 7/1993 | Bushatz et al. | |
| 5,242,412 A | 9/1993 | Blake, III | |
| 5,290,304 A | 3/1994 | Storace | |
| 5,299,813 A | 4/1994 | McKenna | |
| 5,300,033 A | 4/1994 | Miller | |
| 5,300,036 A | 4/1994 | Mueller et al. | |
| 5,308,336 A | 5/1994 | Hart et al. | |
| 5,342,315 A | 8/1994 | Rowe et al. | |
| 5,350,364 A * | 9/1994 | Stephens et al. | 604/167 |
| 5,385,553 A | 1/1995 | Hart et al. | |
| 5,395,342 A | 3/1995 | Yoon | |
| 5,407,433 A | 4/1995 | Loomas | |
| 5,411,483 A | 5/1995 | Loomas et al. | |
| 5,463,010 A * | 10/1995 | Hu et al. | 528/25 |
| 5,496,280 A | 3/1996 | Vandenbroek et al. | |
| 5,545,142 A | 8/1996 | Stephens et al. | |
| 5,603,702 A | 2/1997 | Smith et al. | |
| 5,613,954 A | 3/1997 | Nelson et al. | |
| 5,628,732 A * | 5/1997 | Antoon, Jr. et al. | 604/167 |
| 5,634,908 A | 6/1997 | Loomas | |
| 5,709,664 A | 1/1998 | Vandenbroek et al. | |
| 5,752,938 A | 5/1998 | Flatland et al. | |
| 5,807,338 A * | 9/1998 | Smith | 604/164 |
| 5,827,228 A | 10/1998 | Rowe | |
| 5,865,807 A * | 2/1999 | Blake, III | 604/167 |
| 5,868,714 A | 2/1999 | Danks | |
| 6,004,326 A * | 12/1999 | Castro et al. | 606/99 |
| RE36,702 E | 5/2000 | Green et al. | |
| 6,079,692 A * | 6/2000 | Powell | 251/61.1 |
| 6,228,061 B1 * | 5/2001 | Flatland et al. | 604/167.06 |
| 6,354,602 B1 * | 3/2002 | Oldenburg | 277/630 |
| 6,482,181 B1 * | 11/2002 | Racenet et al. | 604/167.06 |

\* cited by examiner

TROCAR SEAL SYSTEM

This application is a continuation of U.S. patent application Ser. No. 09/527,955, filed on Mar. 9, 2000, which claims priority from PCT International Application No. PCT/US98/08968, filed May 1, 1998, and U.S. Provisional Application Serial No. 60/045,412, filed May 2, 1997, all of which are incorporated herein by reference in their entirety.

BACKGROUND

1. Technical Field

The present disclosure relates to seal systems of the type adapted to allow the introduction of a surgical instrument into a patient's body. In particular, the disclosure relates to a seal system to be used in combination with a cannula assembly where the cannula assembly is intended for insertion into a patient's body and an instrument is inserted into the patient's body through the cannula.

2. Background of Related Art

Laparoscopic procedures are performed in the interior of the abdomen through a small incision, e.g., through narrow endoscopic tubes or cannulas inserted through a small entrance incision in the skin. Minimally invasive procedures are performed elsewhere in the body, e.g., in the chest, and are often generally referred to as "endoscopic" procedures. Minimally invasive or endoscopic procedures generally require that any instrumentation inserted into the body be sealed, i.e. provisions must be made to ensure that gases do not enter or exit the body through the endoscopic incision as, for example, in surgical procedures in which the surgical region is insufflated. Moreover, endoscopic procedures often require the surgeon to act on organs, tissues, and vessels far removed from the incision, thereby requiring that any instruments used in such procedures be relatively long and narrow.

For such procedures, the introduction of a tube into certain anatomical cavities such as the abdominal cavity is usually accomplished by use of a system incorporating a trocar and cannula assembly. A cannula assembly is formed of a cannula attached to a cannula housing which generally includes seal assembly adapted to maintain a seal across the opening of the seal assembly both with and without an instrument inserted therethrough. Since the cannula is in direct communication with the internal portion of the seal assembly, insertion of the cannula into an opening in the patient's body so as to reach the inner abdominal cavity should be adapted to maintain a fluid tight interface between the abdominal cavity and the outside atmosphere.

Since minimally invasive surgical procedures in the abdominal cavity of the body generally require insufflating gases to raise the cavity wall away from vital organs, the procedure is usually initiated by use of a Verres needle through which a gas is introduced into the body cavity. The gas provides a slight pressure which raises the wall surface of the peritoneum away from the vital organs thereby providing an adequate region in which to operate. Thereafter, a trocar assembly which includes a cannula and a trocar or obturator is inserted within the cannula to puncture the peritoneum, i.e. the inner lining of the abdominal cavity wall. The obturator is removed and laparoscopic or endoscopic surgical instruments may then be inserted through the cannula to perform surgery within the abdominal cavity. The cannula may also be utilized for introducing tubes into the body as for drainage purposes, for specimen removal, for diagnostic evaluations, or the like.

In view of the need to maintain the atmospheric integrity of the inner area of the cavity, a seal assembly for a cannula which permits introduction of an obturator and a wide range of surgical instruments and which maintains the atmospheric integrity of the inner area of the cavity is desirable. Generally, in the context of insufflatory, minimally invasive surgical procedures, cannula assemblies include structure(s) that satisfy two sealing requirements. The first requirement is to provide a substantially fluid tight seal when an instrument is not present in the cannula. The second requirement is to provide a substantially fluid tight seal when an instrument is being introduced into or already is present in the cannula. In this regard, there have been a number of attempts in the prior art to provide such sealing requirements.

U.S. Pat. No. 4,655,752 to Honkanen et al. teaches a cannula including a housing and first and second seal members. The first seal member is conically tapered toward the bottom of the housing and has a circular opening in its center, while the second seal is conically tapered and cup shaped. The second seal includes at least one slit to allow for the passage of instruments.

U.S. Pat. No. 4,929,235 to Merry et al. teaches a self-sealing catheter introducer having a sealing mechanism to prevent blood or fluid leakage. The sealing mechanism includes a planar sealing element having a slit and a conical sealing element. The sealing elements are each adapted to surround a tube.

U.S. Pat. Nos. 4,874,377 and 5,064,416 to Newgard et al. relate to a self-occluding intravascular cannula assembly in which an elastomeric valving member is positioned transversely to a housing and is peripherally compressed to cause displacement, distortion and/or rheological flow of the elastomeric material. A frustoconical dilator projection cooperates with the elastomeric valving member in moving the valving member to a non-occluding position.

U.S. Pat. No. 5,300,033 to Miller suggests a valve construction including an elastic body having a cylindrical wall with first and second walls formed integrally with the cylindrical wall. The second wall includes a slit to permit passage of a surgical instrument and first and second leaflets which define the slit. The leaflets are thicker in cross section to provide an additional closing force at the slit.

A disadvantage of several known seal systems for cannulas concerns the difficulty encountered in inserting and advancing the surgical instrument through the seal unit. In particular, since known elastomeric seal members are designed to form and maintain a fluid tight seal about the instrument, the aperture or slit within the seal through which the instrument is passed is of relatively small or narrow dimension. Further, portions of the seal member defining the aperture are generally thick in cross-section to provide a sufficient closing force of the seal about the instrument. see, e.g., U.S. Pat. No. 5,300,033. As a consequence of these design considerations, the level of force needed to insert and advance the instrument through the seal aperture is increased, thereby requiring awkward maneuvering on the surgeon's behalf to appropriately position the instrument for the desired surgery. Moreover, known seal systems are generally ineffectual in accommodating instruments of differing diameter while maintaining acceptable insertion forces and facilitating the range of desired surgical manipulations, e.g., angular instrument movements and specimen removal.

Accordingly, the present disclosure obviates the disadvantages of the prior art by providing a seal unit or assembly for a cannula assembly, which is capable of forming and maintaining a tight seal about instruments of varying diameters inserted through the cannula and which incorporates structure to enhance and facilitate passage of the instrument through the seal unit.

SUMMARY

The present disclosure provides a seal assembly for reception of an elongated surgical instrument, which comprises a body having at least one opening configured and dimensioned to permit entry of an elongated surgical instrument and defining a central longitudinal axis; a seal member formed of a resilient material and defining an aperture therein, the aperture being configured and dimensioned such that insertion of the surgical instrument into the aperture causes the resilient material defining the aperture to resiliently contact the outer surface of the surgical instrument in a substantially fluid tight manner; and a fabric layer juxtaposed relative to the resilient material.

The seal assembly may further include a coating applied to the seal member to reduce friction between the seal member and surgical instrumentation inserted therein. The coating is preferably a hydrocyclosiloxane membrane prepared by plasma polymerization process.

In one aspect of the presently disclosed seal assembly a ring member is secured to the seal member and includes a dampening element disposed between a surface of the ring member and a surface of the body.

BRIEF DESCRIPTION OF THE DRAWINGS

Various embodiments are described herein below with reference to the drawings wherein.

DETAILED DESCRIPTION OF PREFERRED EMBODIMENTS

Figure 1:
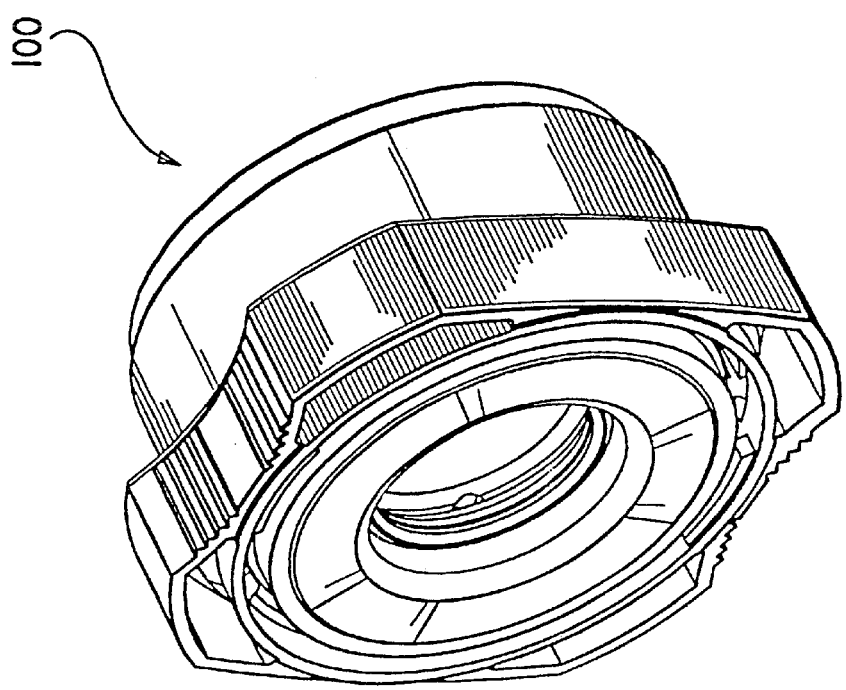
FIG. 1 is a perspective view of one embodiment of a seal assembly constructed in accordance with the present disclosure.
Figure 2:
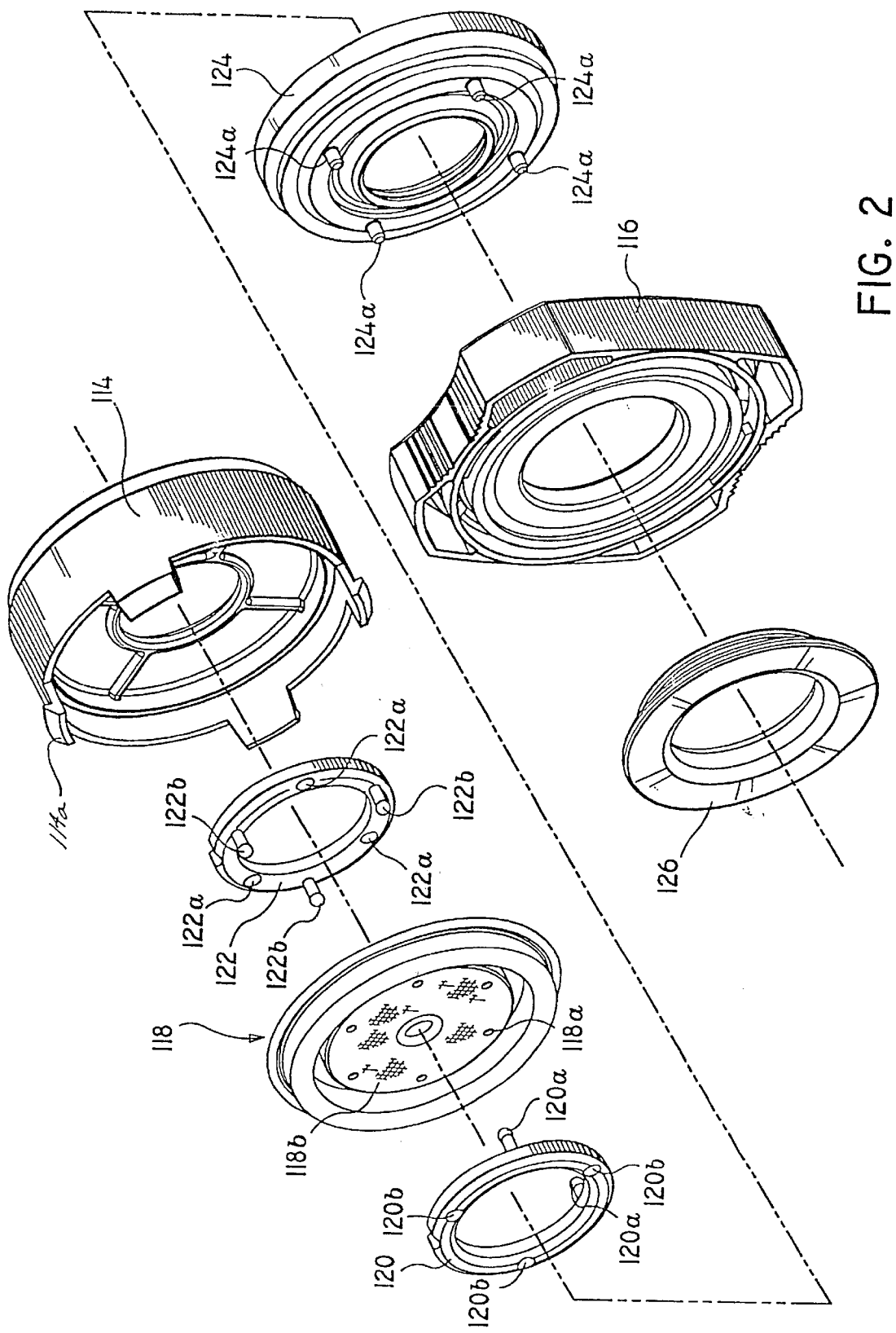
FIG. 2 is a perspective view with parts separated showing the various structural components of the seal assembly embodiment of FIG. 1.
Figure 3:
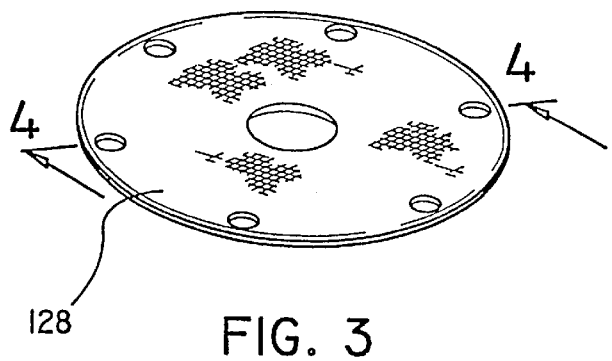
FIG. 3 is a perspective view of a fabric portion for incorporation into the seal element of the embodiment of FIG. 1.
Figure 4:
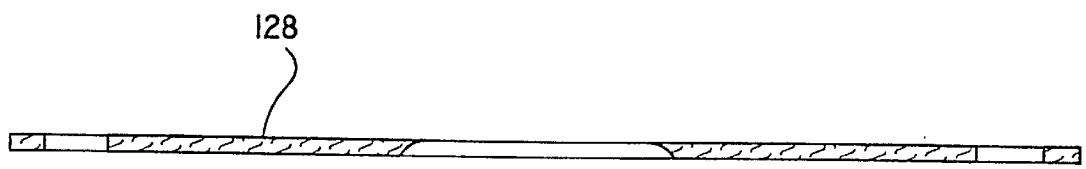
FIG. 4 is a cross-sectional view taken along section line 4—4 of FIG. 3.
Figure 5:
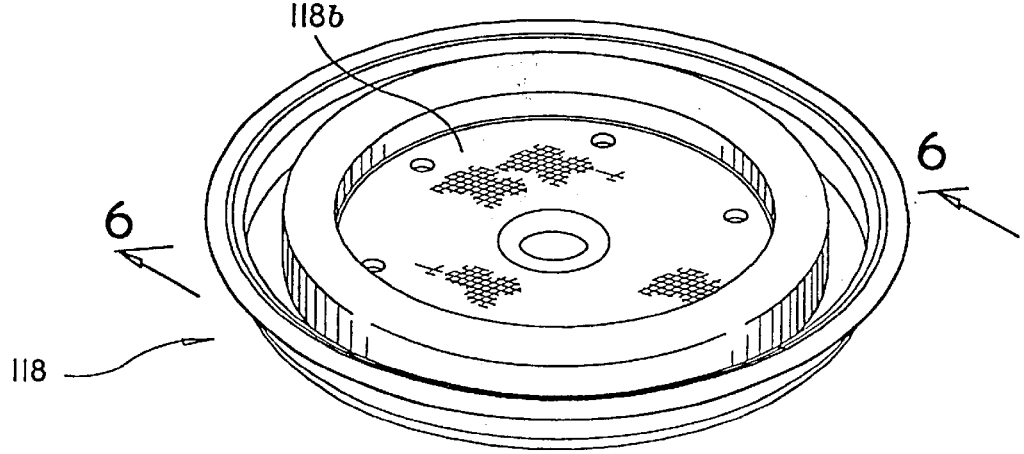
FIG. 5 is a perspective view of a fully formed seal member for the seal assembly of FIG. 1.

Referring now in detail to the drawing figures in which like reference numerals identify similar or identical elements, a first embodiment of the seal assembly of the present disclosure is illustrated in FIGS. 1–9, and is designated generally as seal assembly 100.

The presently disclosed seal assembly embodiments contemplate the introduction of various types of surgical instruments adapted for insertion through an elongated trocar assembly. Examples of such instruments include clip appliers, graspers, dissectors, retractors, staplers, laser fibers, photographic devices, endoscopes and laparoscopes, tubes, and the like. Such instruments are collectively referred to herein as "instruments".

A two part ring assembly which includes ring members 120 and 122 are snap fitted together on either side of seal member 118. Ring member 120 is disposed adjacent the distally facing surface of seal member 118 and ring member 122 is disposed on the proximally facing side of seal member 118. Ring 120 is provided with holes 120b and posts 120a which are alternately disposed around the ring and are aligned with holes 118a on seal member 118. Ring 122 is provided with posts 122b and holes 122a which mate with holes 120a and posts 120b of ring member 120, respectively by snap fitting together thereby surrounding inner section 118b. Although rings 120 and 122 are shown having alternating holes and posts, one of the rings could have all holes formed therein while the other ring could have all posts aligned with the holes of the other ring. Additionally, greater or fewer holes and posts may be utilized to secure the two rings together.

Figure 7:
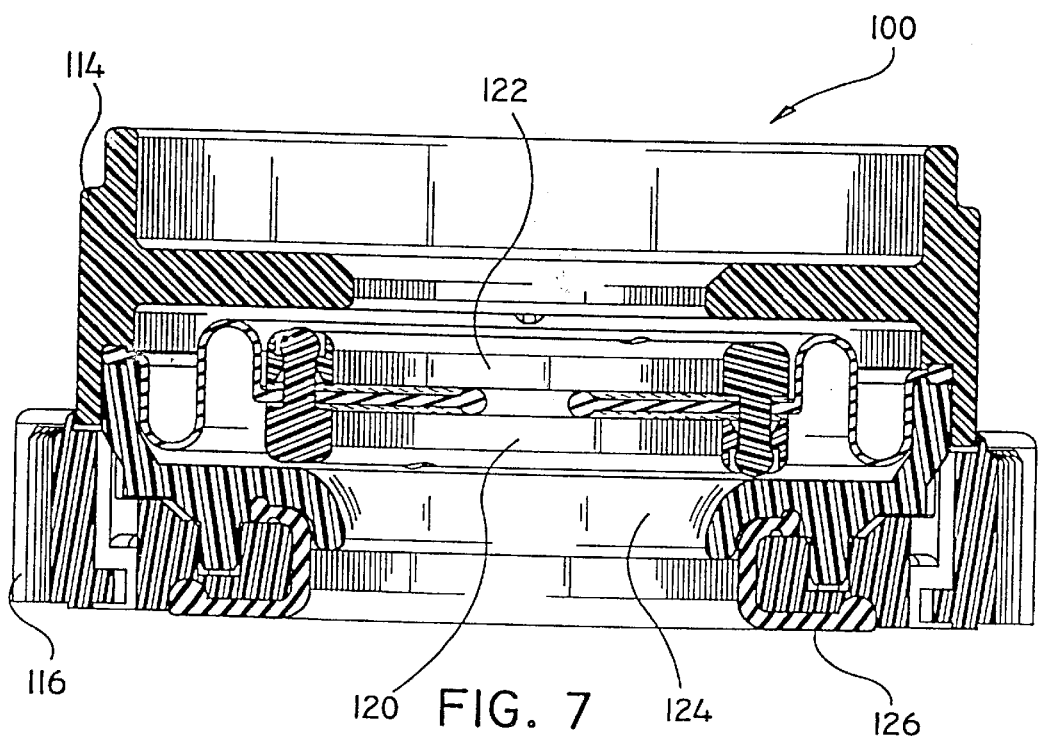
FIG. 7 is a cross-sectional view of the seal assembly of FIG. 1.

A seal clamp 124 is provided within the housing component 114 and 116 and serves to secure the outer periphery of seal member 118 within seal assembly 100 (as best shown in FIG. 7). Seal clamp 124 is provided with four projecting posts 124a which fit within openings (FIG. 7) formed on the proximal side of lower housing 116. Seal clamp 124 also serves to secure a proximal flange of a lower seal 126 which is provided at the distal end of lower housing member 116. Lower seal 126 assists in the securement of seal assembly 100 to cannula assembly 110.

Referring now to FIGS. 3–6, seal member 118 includes a fabric disc-shaped portion 128 which is preferably disposed on both the proximal and distal sides of inner section 118b of seal member 118. Alternatively, fabric section 128 may be disposed on just one of either the proximally facing surface or the distally facing surface of inner portion 118b, as desired. Fabric portion 128 may be of any suitable fabric, for example, a SPANDEX material containing 20% LYCRA available from Milliken.

In one method of forming the composite seal member 118 with fabric portion 128 a raw, i.e., uncured polyisoprene plug is first compressed into a flat state, e.g., a flat sheet of polyisoprene. A single layer of fabric is positioned on top of the flattened polyisoprene sheet and compressed into the uncured rubber by any suitable compression process such as, for example, calendering. If it is desired to have fabric on both sides of seal member 118, this process is repeated on the other side of the polyisoprene sheet. The fabric polyisoprene composite is die cut into circular slugs having an outer diameter and an inner diameter which forms a central aperture. The slugs are placed in a hot compression mold to cure the polyisoprene. This step also serves to extrude the outer portions of seal member 118 which extend outwardly from inner section 118b.

During the above-described process the bleed-through of the polyisoprene material into and/or through the fabric layers is regulated by the density of the fabric selected. A greater degree of bleed-through of polyisoprene provides greater resistance to fraying of the fabric upon repeated insertion of instruments through the seal. However, too much bleed-through of the polyisoprene through the fabric will increase friction forces upon instruments being inserted through seal member 118.

Figure 6:
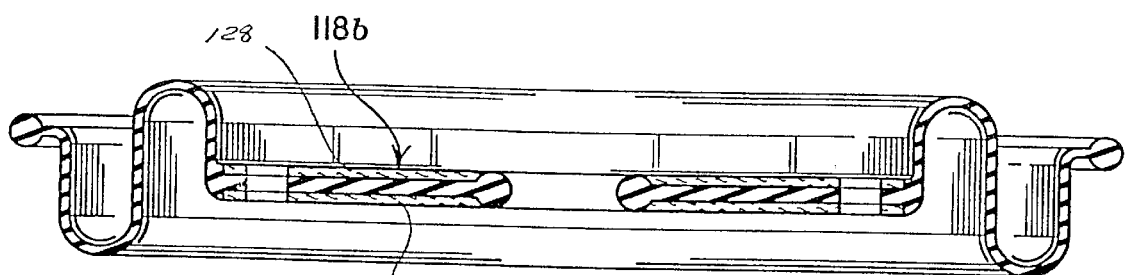
FIG. 6 is a cross-sectional view taken along section line 6—6 of FIG. 5.
Figure 6A:
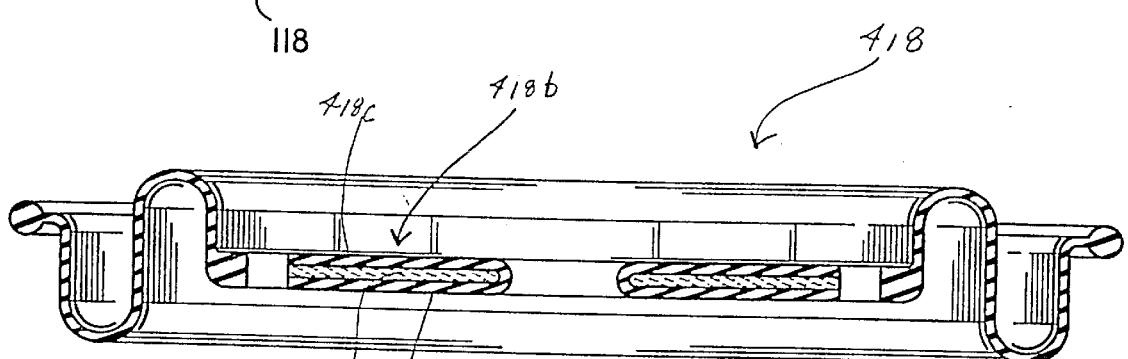
FIG. 6A is an alternative embodiment of the seal element of FIG. 6.

Referring to FIG. 6A, an alternative embodiment of seal member 118 is shown as seal member 418. Seal member 418 is the same as seal member 118 in most aspects except that inner section 418b is formed to have fabric layer 428 enveloped between upper and lower polyisoprene layers 418c and 418d.

In order to reduce friction between instruments and the seal member, e.g. seal member 118 or seal member 418, as instruments are inserted through seal assembly 100, a coating may be applied to the seal member. One coating which has been found particularly effective is a hydrocyclosiloxane membrane prepared by plasma polymerization process. Such a coating is available from Innerdyne, Inc. of Salt Lake City, Utah, U.S.A., and is disclosed in U.S. Pat. No. 5,463,010 which issued to Hu et al. on Oct. 31, 1995, the entire contents of which are hereby incorporated by reference.

Figure 8:
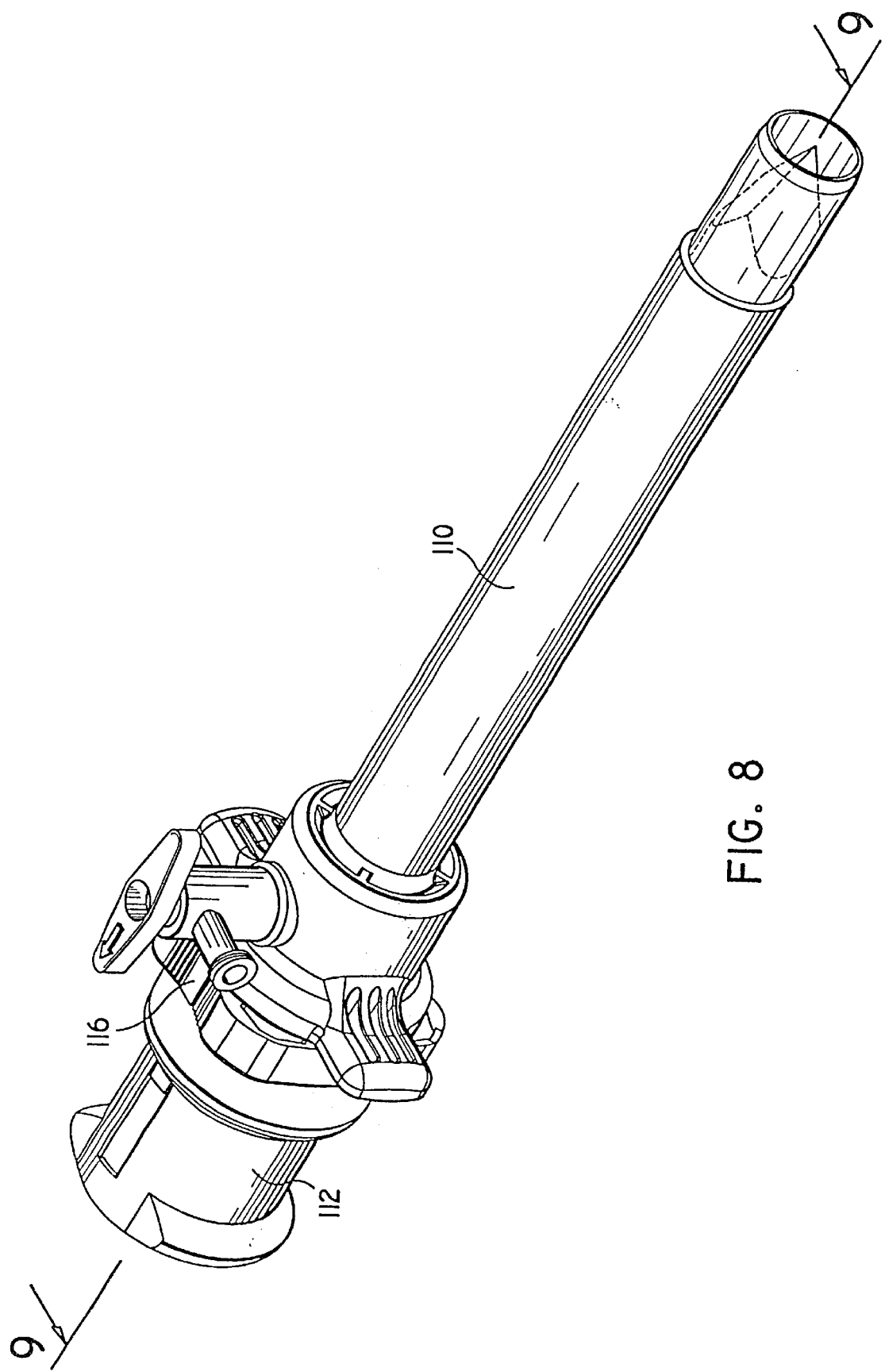
FIG. 8 is a perspective view of a trocar assembly having the seal assembly of FIG. 1 removably installed thereon.

Referring to FIGS. 7 and 8, seal assembly 100 is used in combination with a conventional trocar assembly which includes a cannula assembly 110 and a trocar obturator 112. Examples of trocar assemblies in which the present seal assembly may be utilized are disclosed in U.S. Pat. No. 5,603,702 which issued on Feb. 18, 1997 to Smith et al. and U.S. application Ser. No. 08/546,009 filed Oct. 20, 1995 by Smith et al., the entire contents of each of these disclosures are hereby incorporated by reference.

Seal assembly 100, either alone or in combination with a seal unit/seal assembly internal to cannula assembly 110, provides a substantial seal between a body cavity of a patient and the outside atmosphere both during and subsequent to insertion of an instrument through the cannula. In this manner, insufflation gases are prevented from escaping through the trocar assembly to the outside environment. Seal assembly 100 is capable of accommodating instruments of varying diameter, e.g., from about 5 mm to about 12 mm, while providing a fluid tight seal with the outer diameter of each instrument. The versatility of the presently disclosed seal assembly embodiments greatly facilitate endoscopic surgery, wherein a variety of instruments having different diameters are often needed during a single surgical procedure.

Seal assembly 100 is preferably detachably mountable to the proximal end of cannula assembly 110. Thus, the surgeon can remove the seal assembly 100 from the cannula assembly 110 at any time during the surgical procedure and, similarly, mount the seal assembly 100 to the cannula when desired in order to provide a sealing engagement with an instrument to be inserted through the cannula. In addition, seal assembly 100 may be readily adapted for mounting to conventional cannulas of differing structures. The detachability of seal assembly 100 from cannula assembly 110 facilitates specimen removal through cannula assembly 110. Seal assembly 100 includes a housing which is formed by the snap fitting together of end cap 114 and lower housing member 116. Preferably the housing components of seal assembly 100 are formed of a polycarbonate material such as ABS available from the General Electric Company.

Figure 9:
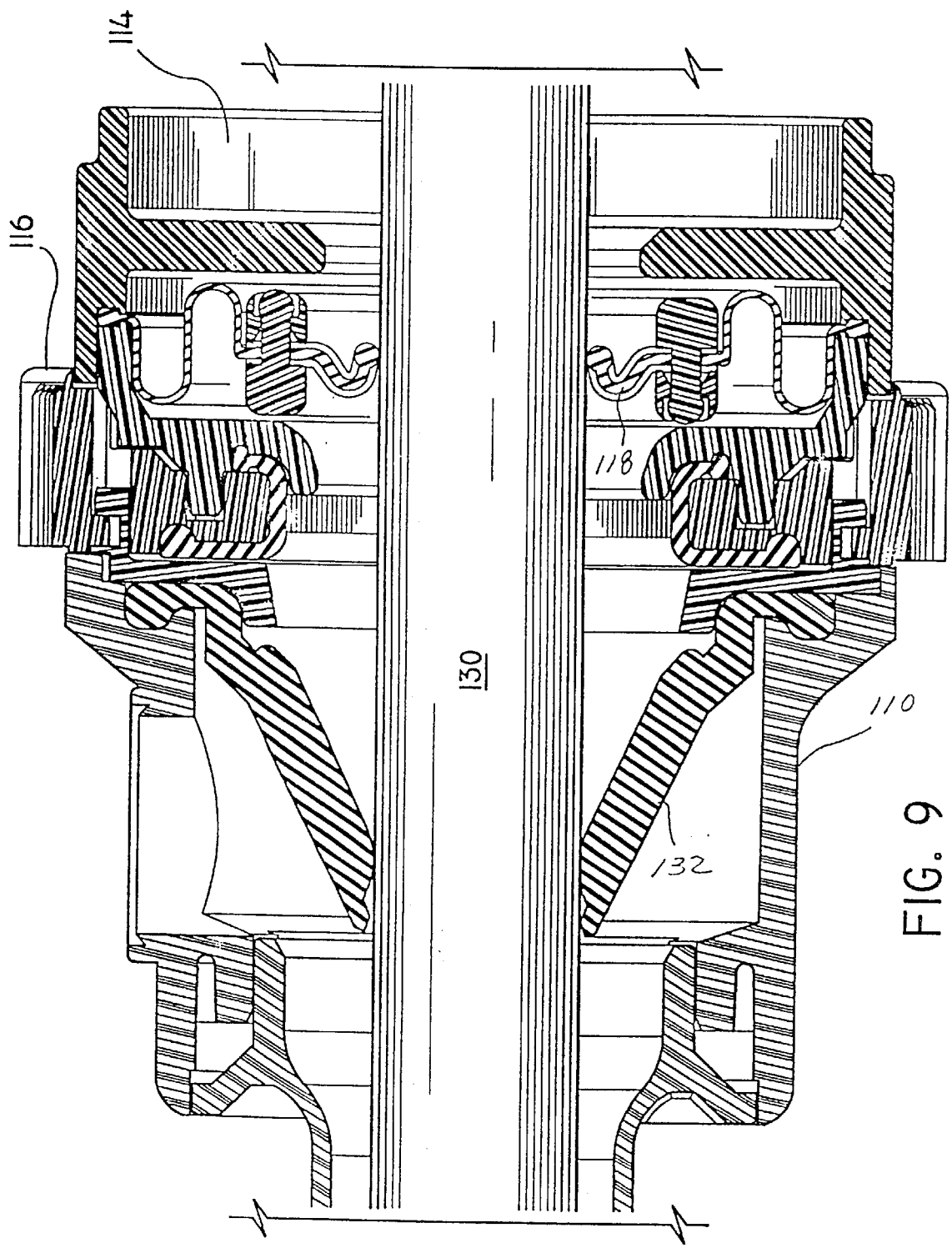
FIG. 9 is a partial cross-sectional view showing the seal body housing. taken along section line 9—9 of FIG. 8.

FIG. 9 shows an instrument having a shaft 130 inserted through seal assembly 100 and a duck bill valve or "zero" seal valve 132 which prevents the escape of insufflation gases in the absence of an instrument in the trocar assembly. As shown in FIG. 9, seal member 118 provides a seal about the periphery of shaft 130.

Figure 10:
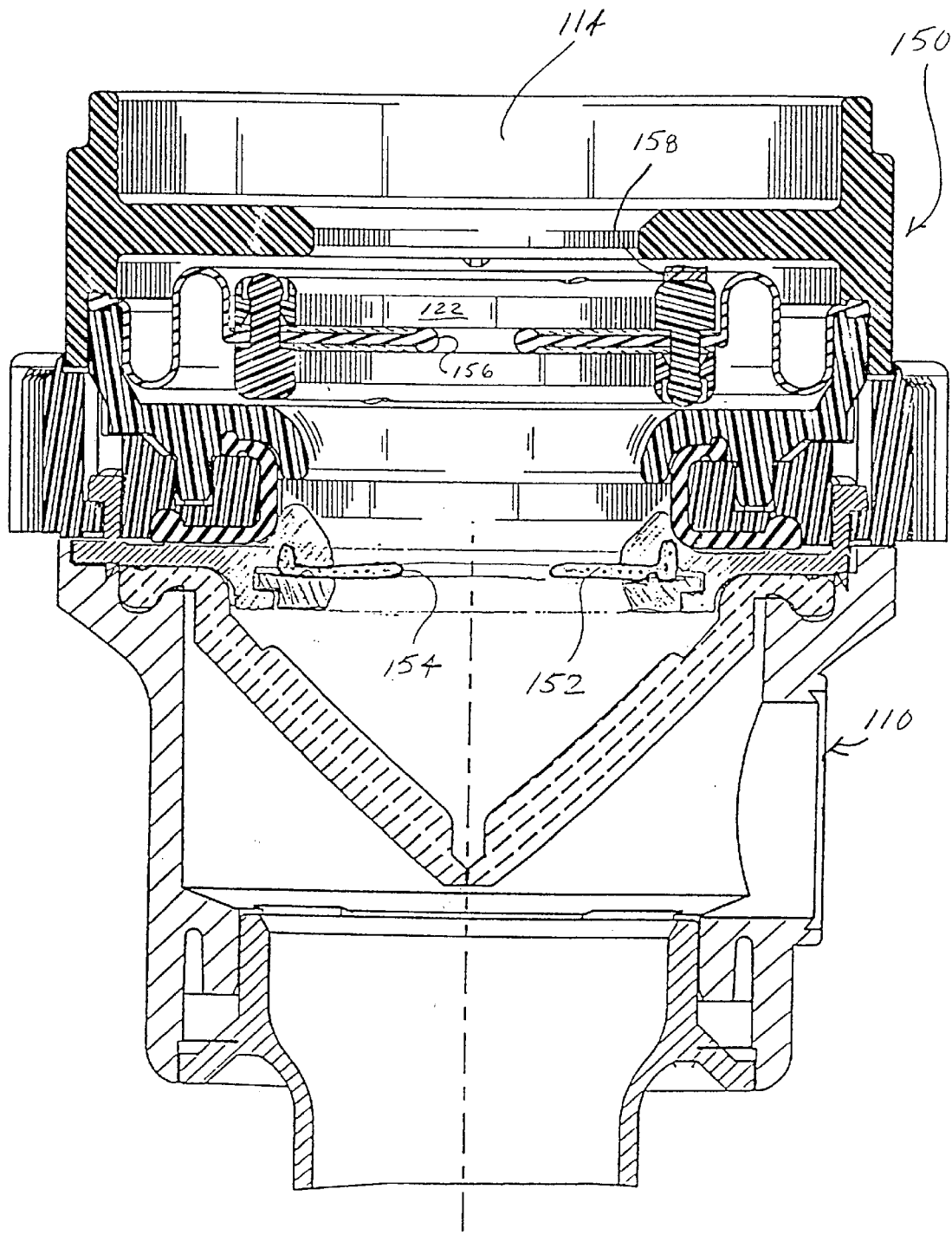
FIG. 10 is an alternative embodiment of the seal assembly of the present disclosure.

Referring to FIG. 10, an alternate embodiment of seal assembly 100 is designated generally as seal assembly 150. Seal assembly 150 is the same as seal assembly 100 except that an inner planar seal member 152 is disposed in the distal end of seal assembly 100 to provide additional sealing capability for instruments having larger diameters. Seal element 152 has an aperture 154 which has a diameter larger than the diameter of aperture 156 of seal member 118. A further feature illustrated in FIG. 10 is a dampening member such as pad 158 which is secured to the proximal surface of ring 122 to dampen the sound created by the impact of the proximal surface of ring 122 with the inner distal facing surface of housing component 114. Other dampening member configurations are also contemplated. For example, ring 122 may be over-molded with material such as polyisoprene so as to envelope part or all of the ring thereby forming a bumper between the ring and the housing component.

Figure 11:
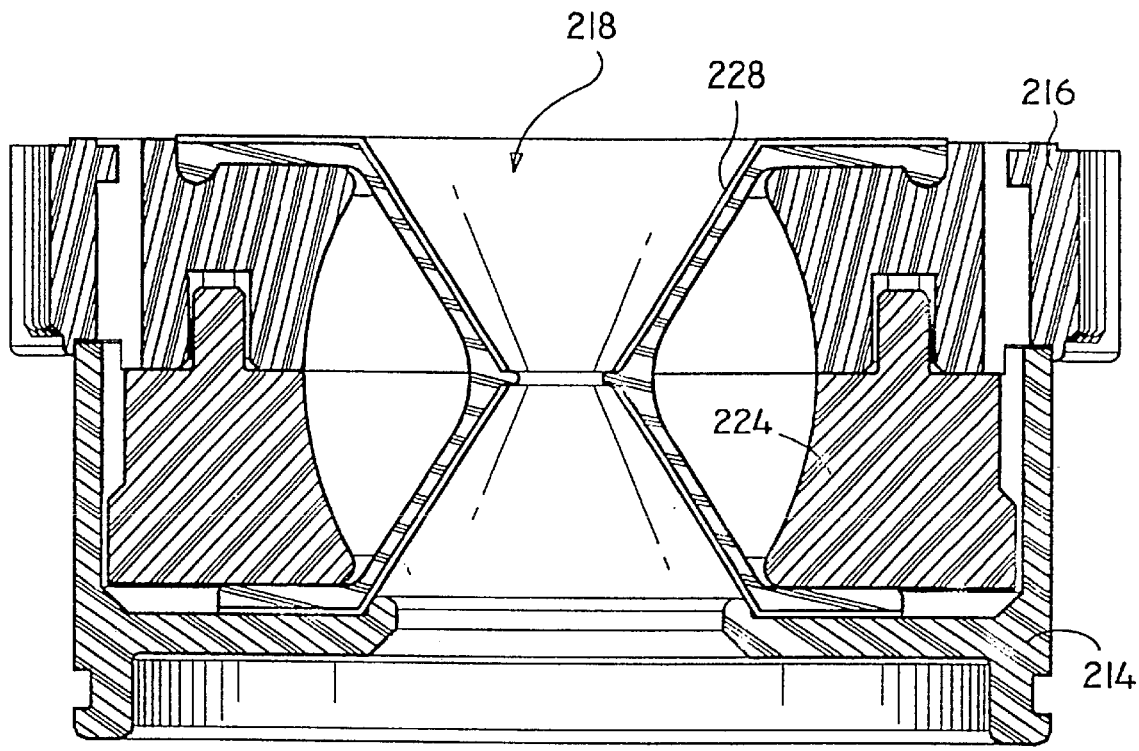
FIG. 11 is a cross-sectional view of a further embodiment of the seal assembly constructed in accordance with the present disclosure.
Figure 12:
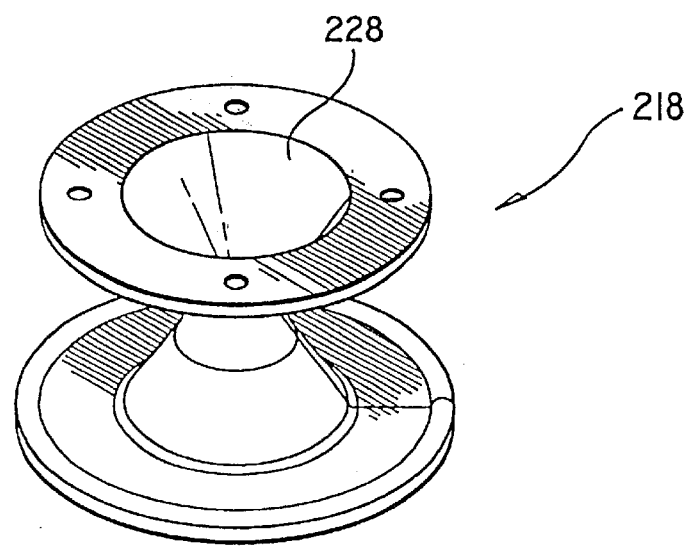
FIG. 12 is a perspective view of the seal assembly of FIG. 11.
Figure 13:
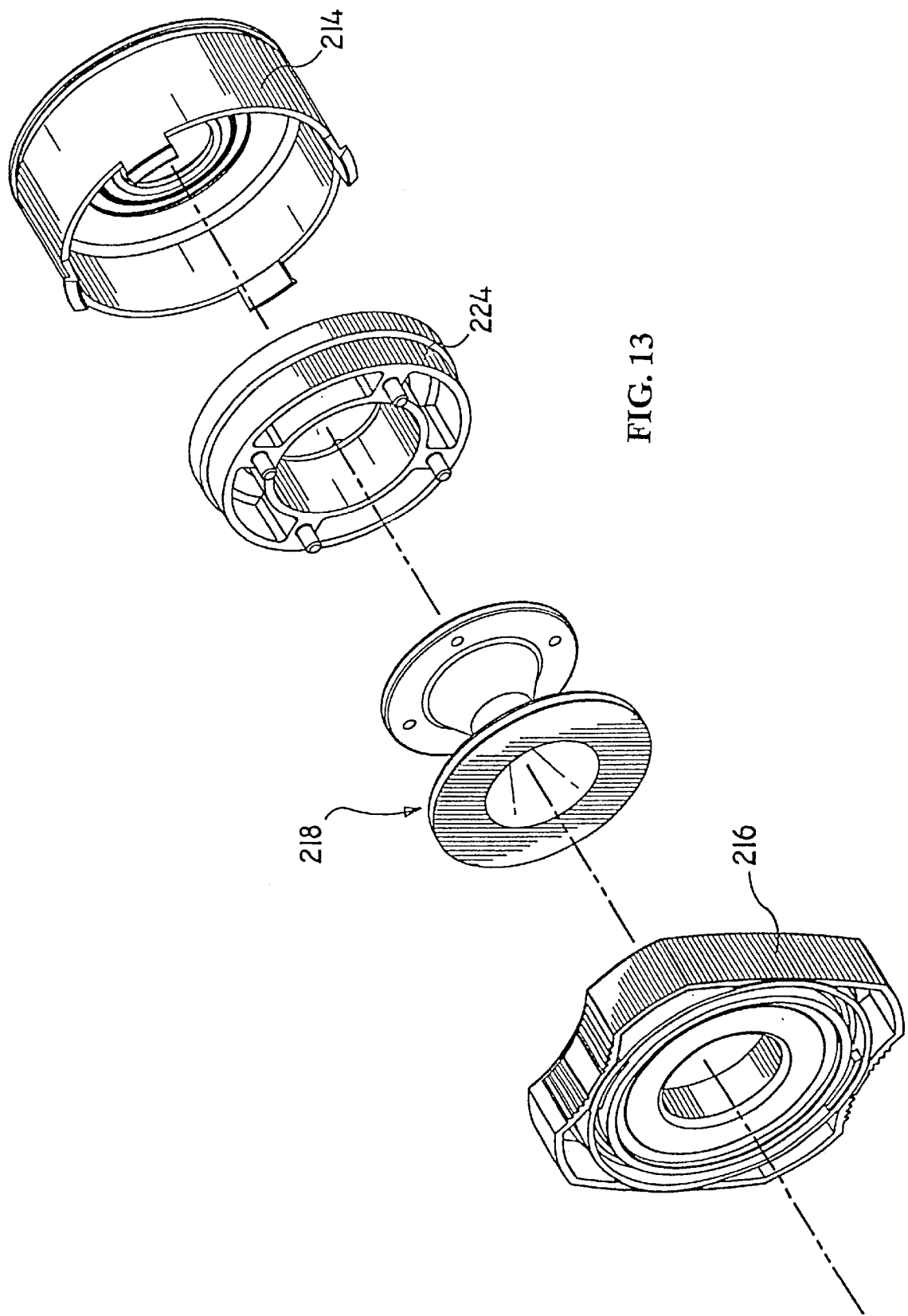
FIG. 13 is a perspective view with parts separated of the seal assembly embodiment of FIG. 11.

Referring to FIGS. 11–13, a further embodiment of a seal assembly generally designated as seal assembly 200 is shown throughout the several views. Seal member 218 is configured in an hourglass shape and preferably includes the fabric portion 228 formed as part of seal member 218 in a similar manner as described above. The friction reducing coating of a hydrocyclosiloxane membrane prepared by plasma polymerization process noted above may also be utilized to coat the surfaces of seal member 218.

Figure 14:
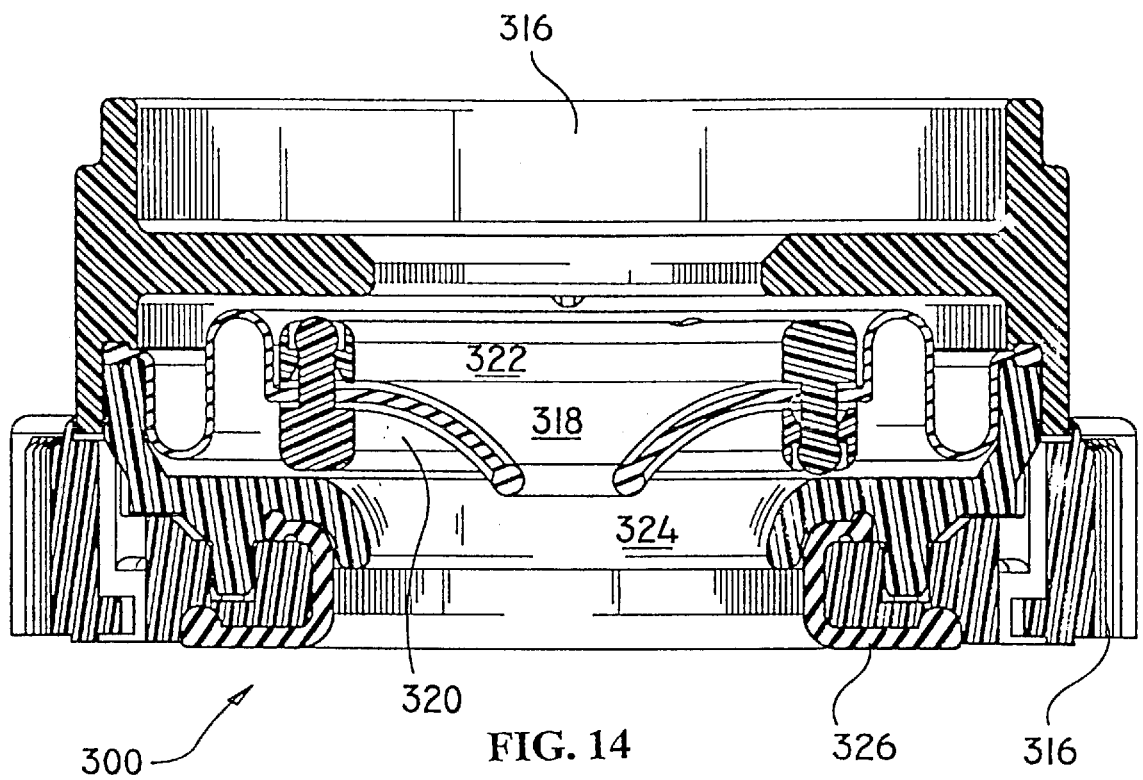
FIG. 14 is a cross-sectional view of a further embodiment of the seal assembly constructed in accordance with the present disclosure.
Figure 15:
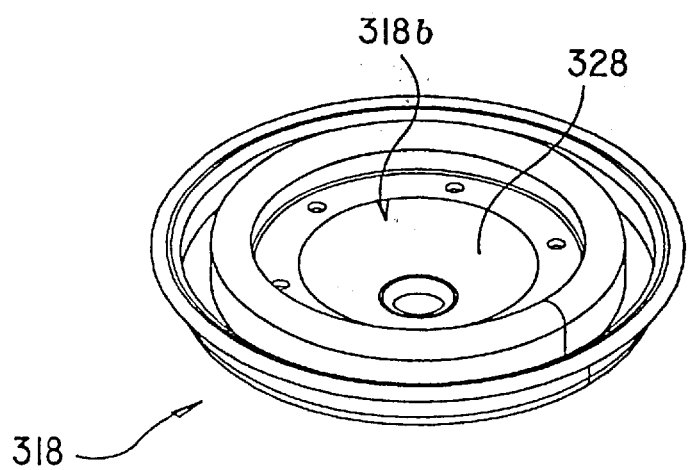
FIG. 15 is a perspective view of the seal member of the seal assembly of FIG. 14.

Referring now to FIGS. 14 and 15, a further embodiment of the seal assembly generally designated as seal assembly 300 is shown. Seal member 318 is similar to seal member 118 except that inner portion 318b is formed in a conical shape with a wider opening directed towards a proximal end of seal assembly 300 and a narrower opening directed towards distal end of seal assembly 300. The friction reducing coating of a hydrocyclosiloxane membrane prepared by plasma polymerization process noted above may also be utilized to coat the surfaces of seal member 318.

It will be understood that various modifications may be made to the embodiments shown herein. Therefore, the above description should not be construed as limiting, but merely as exemplifications of preferred embodiments. Those skilled in the art will envision other modifications within the scope and spirit of the presently disclosed seal assemblies.

What is claimed is:

1. A seal assembly for reception of an elongated surgical instrument, which comprises:

a body having at least one opening configured and dimensioned to permit entry of an elongated surgical instrument and defining a central longitudinal axis;

a seal member formed of a resilient material and defining an aperture therein, the aperture being configured and dimensioned such that insertion of the surgical instrument into the aperture causes the resilient material defining the aperture to resiliently contact the outer surface of the surgical instrument in a substantially fluid tight manner; and a fabric layer juxtaposed relative to the resilient material.

2. A seal assembly for reception of an elongated surgical instrument according to claim 1, which further comprises a coating applied to the seal member to reduce friction between the seal member and surgical instrumentation inserted therein.

3. A seal assembly for reception of an elongated surgical instrument according to claim 2, wherein the coating is a hydrocyclosiloxane membrane prepared by plasma polymerization process.

4. A seal assembly for reception of an elongated surgical instrument according to claim 1, which further comprises a ring member secured to the seal member and having a dampening element disposed between a surface of the ring member and a surface of the body.

5. A seal assembly comprising:

a housing having a throughbore; and a seal member supported within the housing, the seal member being formed of a resilient material, the resilient material having a top surface and a bottom surface, the seal member having fabric material positioned adjacent the resilient material and having an opening formed therein aligned with the throughbore in the housing.

6. A seal assembly according to claim 5, wherein the seal member has fabric material positioned on both the top and bottom surfaces of the resilient material.

7. A seal assembly according to claim 5, wherein the resilient material is polyisoprene.

8. A seal assembly according to claim 5, wherein the seal member includes a coating of material for reducing friction between the seal member and an instrument inserted through the seal member.

9. A seal assembly according to claim 8, wherein the coating is a hydrocyclosiloxane membrane.

10. A seal assembly according to claim 5, further including a ring assembly including a first ring member supported on the top surface of the seal member and a second ring member supported on the bottom surface of the seal member.

11. A seal assembly according to claim 10, wherein the first and second ring members are adapted to be snap-fitted together.

12. A seal assembly according to claim 5, wherein the housing includes an upper housing component and a lower housing component, the upper and lower housing components being positioned on opposite sides of the seal member.

13. A seal assembly according to claim 5, wherein the fabric material is positioned between layers of resilient material.

14. A seal assembly according to claim 5, wherein the seal assembly is adapted to releasably engage a cannula assembly.

15. A seal assembly according to claim 5, wherein the seal member has an hourglass configuration.

16. A seal assembly according to claim 5, wherein the seal member has a conical configuration.

17. A seal assembly according to claim 5, further including a second seal member, the second seal member having an opening formed therein having a diameter which is larger than the opening in the first seal member.

18. A seal assembly according to claim 10, further including a clamping element positioned between the ring assembly and the housing.

* * * * *